United States Patent [19]

McBride et al.

[11] 4,040,790
[45] Aug. 9, 1977

[54] MOISTURE AND RUST DETECTOR FOR HYDRAULIC CONTROL SYSTEMS

[75] Inventors: Robert B. McBride, Troy; Phillip J. Tiberio, Schenectady, both of N.Y.

[73] Assignee: General Electric Company, Schenectady, N.Y.

[21] Appl. No.: 709,793

[22] Filed: July 29, 1976

[51] Int. Cl.² .................... G01N 17/00; G01F 15/00
[52] U.S. Cl. ................... 23/253 C; 73/328; 116/118 A; 415/118; 417/63
[58] Field of Search ............. 415/118; 417/63; 418/2; 73/326, 328; 318/643; 23/253 C, 230 C

[56] References Cited

U.S. PATENT DOCUMENTS

| | | | |
|---|---|---|---|
| 1,769,463 | 7/1930 | Rice | 23/253 C |
| 2,763,534 | 9/1956 | Campbell | 23/253 C |
| 2,910,940 | 11/1959 | Colman et al. | 417/63 |
| 2,976,123 | 3/1961 | Marsh et al. | 23/253 C |

*Primary Examiner*—C. J. Husar
*Attorney, Agent, or Firm*—John F. Ahern; James W. Mitchell

[57] ABSTRACT

Steam turbine hydraulic control system utilizing hydraulic fluid more dense than water accumulates any moisture present as vapor over the fluid reservoir. A detector for such moisture vapor which indicates unacceptable moisture admixed with the hydraulic fluid is connected in gas flow relationship with fluid reservoir at a level above the fluid level. A detector element, preferably a polished ferrous metal plate which readily rusts in the presence of water vapor, is maintained in a detector chamber having transparent portions, allowing for visual inspection to detect rusting and, hence, the presence of moisture in the hydraulic fluid.

10 Claims, 2 Drawing Figures

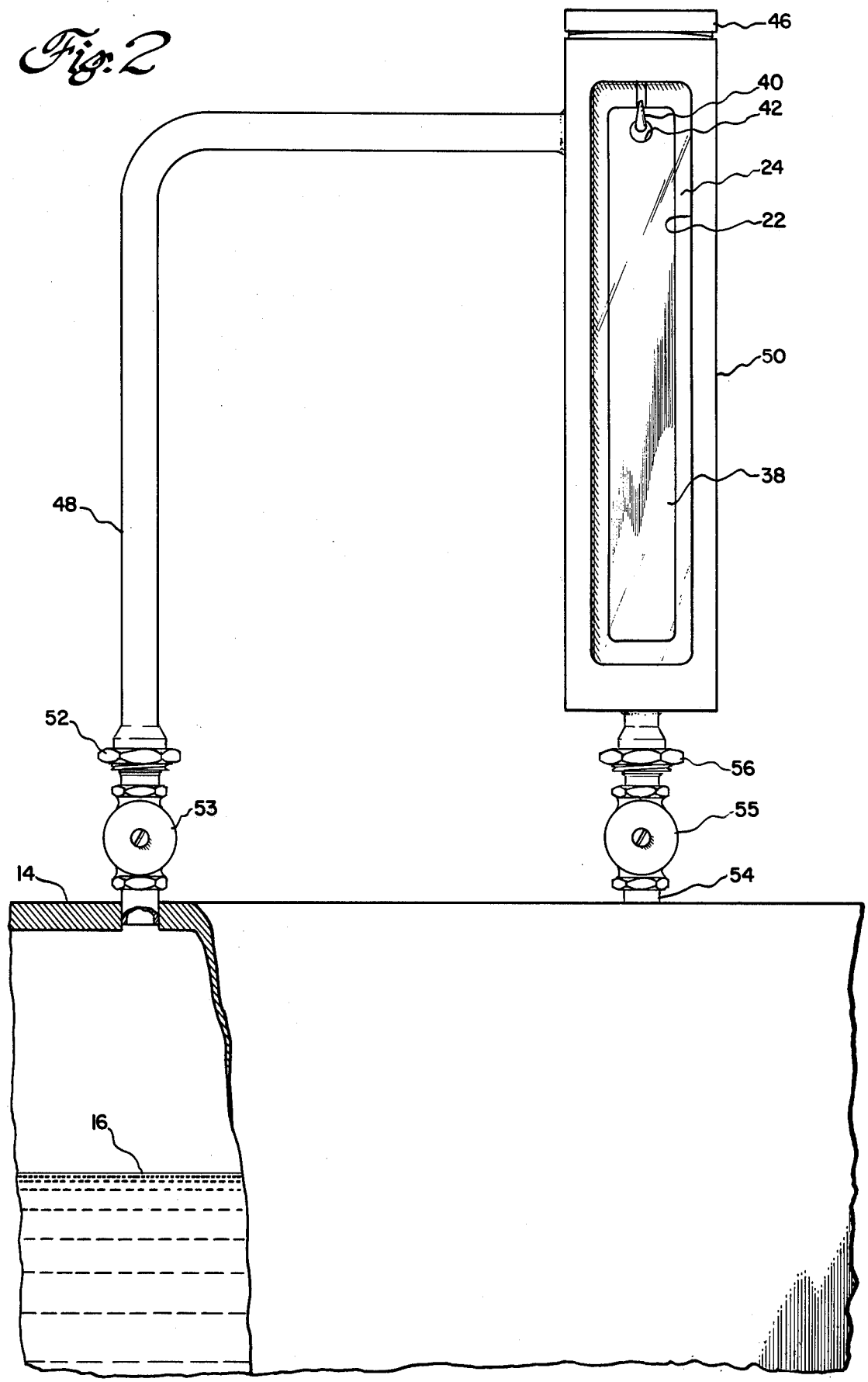

MOISTURE AND RUST DETECTOR FOR HYDRAULIC CONTROL SYSTEMS

BACKGROUND OF THE INVENTION

1. Field of the Invention

This invention relates to hydraulic control systems for steam turbines and more particularly to devices for detecting the presence of moisture in such systems.

2. Description of the Prior Art

The hydraulic system for a steam turbine, for example, as for instance an Electrohydraulic Control (EHC) system includes a fluid reservoir, pumps, filters, accumulators, valves and water-cooled heat exchangers arranged in a closed loop system. A faulty heat exchanger in such a system can result in the introduction of water into the system. The presence of even a small amount of water in an EHC system can result in rusting of the valves and thereby cause serious control malfunctions.

The danger of rust, and hence of possible control malfunctions in hydraulic control systems, is increased because of the phosphate ester fluid now normally employed as the hydraulic fluid in such systems in lieu of other fluids such as petroleum oils. This phosphate ester fluid is denser than water so that any water present in the system floats on the surface of the control fluid and readily evaporates to moisture at the operating temperature of the system. This moisture then can condense on system components resulting in rusting thereof. Petroleum oils are less dense than water so that with petroleum oils the water would accumulate at the bottom of the reservoir and its potential for causing moisture and rust in the EHC system is less.

Water is also about ten times more soluble in phosphate ester fluids than in petroleum oils and this accentuates the rusting problem during shut-down of the turbines. Under shut-down conditions, the temperature drops and the water tends to come out of solution. The resulting moisture tends to condense on components of the system where the rusting can cause damage and malfunction.

Because of the danger of rusting, programs have been instituted for regular sampling of the fluid in EHC systems to test the moisture content. Under such programs, a maximum acceptable moisture content is established and samples are taken at regular intervals. These samples are then tested to insure that the moisture content remains below the acceptable level. If a given test shows that the moisture has risen above the acceptable level, steps must be taken to remove the moisture. Such a testing program requires disassembly of at least some component, for example, an inspection cover on the reservoir, in order to obtain access to the fluid, and it requires trained personnel to insure that disassembly and reassembly and testing as to percentage of moisture content are done effectively.

Moreover, even aside from the problems associated with the disassembly and reassembly of components, such programs inherently involve some interval of time between tests, for example, the tests may be made at monthly intervals. Leakage of water into the system a short time after one test could cause significant damage before the time for the next test occurred.

By the present invention the necessity for obtaining access to the reservoir for taking samples of the fluid and the testing of the samples for particular moisture content is obviated and a detector is provided with which relatively untrained personnel can easily and quickly make inspections, on a daily basis, or more frequently if desired, with a minimum of expenditure of time and without the necessity of disassembling and reassembling any component to obtain access to the interior of the system.

It is therefore an object of this invention to provide an improved detector for promptly and easily detecting moisture in a hydraulic control system before any damage to system components can occur.

It is a further object of this invention to provide a detector which permits easy visual inspection by relatively untrained personnel.

It is a further object of this invention to provide a detector which permits visual inspection of a condition indicative of moisture content without the necessity of disassembly and reassembly of any components to obtain access to the interior of the system.

SUMMARY OF THE INVENTION

In carrying out the invention, in one form thereof, a moisture detector is mounted on the fluid reservoir of a hydraulic control system, as for example, an Electrohydraulic Control system. The detector includes an elongated stainless steel case having one or more elongated apertures therein. Each aperture is closed by transparent material, such as glass, which is sealed to the case and provides for viewing the interior of the case. The case is placed in communication with the reservoir by conduits connected to the reservoir above the level of fluid therein and connected to the case near the top and bottom thereof. Within the case and viewable through the aforementioned transparent material is a strip of material, such as low carbon steel, which is highly susceptible to rusting in the presence of moisture. This strip is easily and quickly inspected visually and the presence of moisture in the system, as indicated by rust forming on the strip, is readily and promptly detected.

DESCRIPTION OF THE DRAWINGS

For a better understanding of the invention, reference may be had to the accompanying drawing in which

FIG. 2 is a view of a similar detector mounted on the top of the reservoir.

DESCRIPTION OF THE PREFERRED EMBODIMENT

Figure 1:
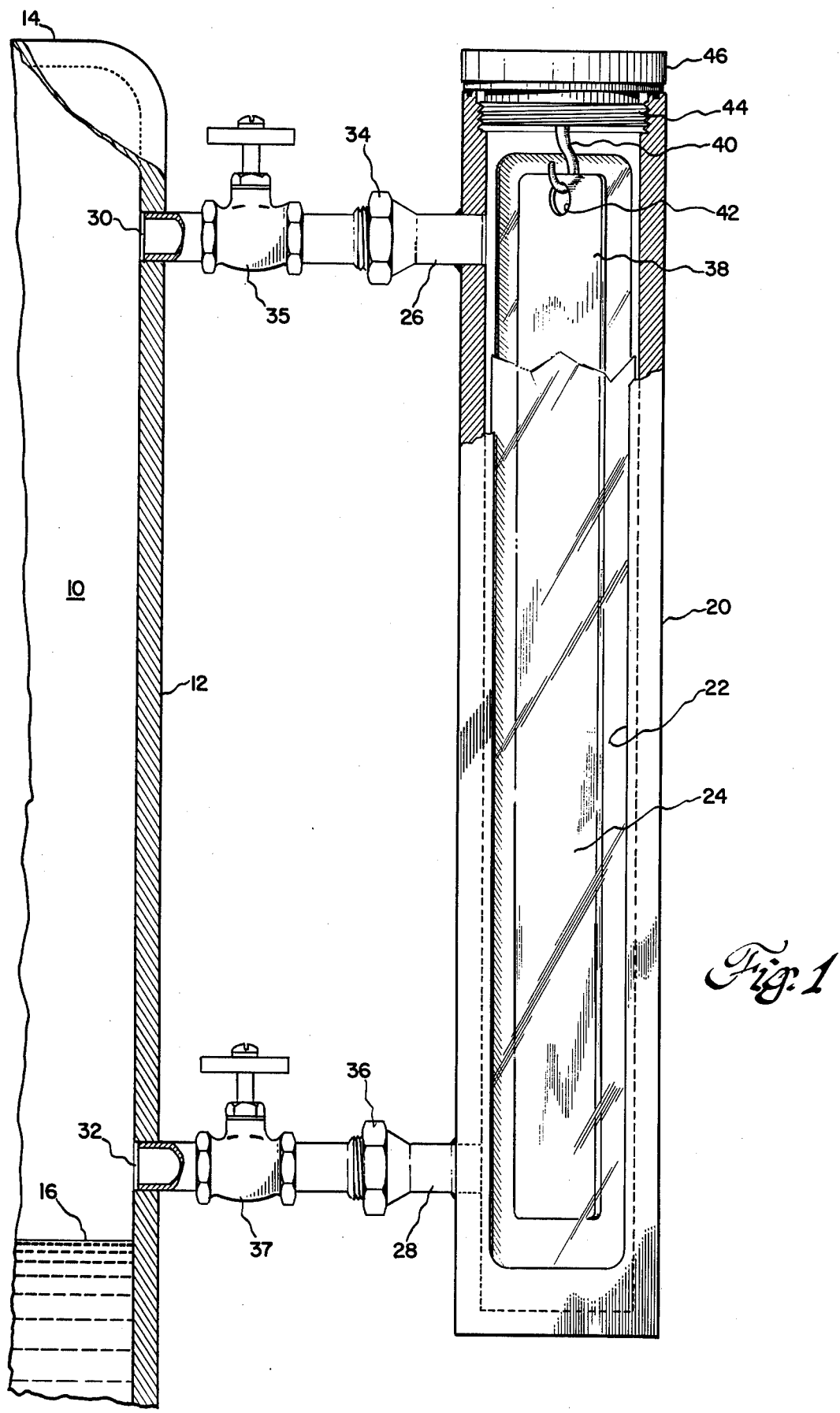
FIG. 1 is an elevation view of a moisture detector mounted on the side of a fluid reservoir of a hydraulic control system.

The moisture detector of the present invention is intended for use with hydraulic control systems. Such systems comprise a number of components including a reservoir for the control fluid, pumps, filters, accumulators, valves and water-cooled heat exchangers arranged in a closed loop system. Particularly where there is a faulty heat exchanger, water may be introduced into the system and the resultant moisture condensing on components of the system can cause rusting which is seriously detrimental to the system. This is a particular problem where the rusting occurs in the valves and may result in serious control malfunctions.

Referring to FIG. 1, there is shown a reservoir 10 for the control fluid. This reservoir includes a side wall 12 and a top wall 14. The reservoir contains hydraulic fluid used in the control system, the fluid being at a level in the reservoir indicated by the numeral 16. The hydraulic fluid now normally employed in such systems is a phosphate ester fluid. This fluid is denser than water and hence water tends to float on the surface of the liquid rather than to collect at the bottom of the reservoir. The water is therefore readily evaporated at the normal operating temperature of 130° F and can then condense on system components with resultant rusting thereof. Moreover, water is much more soluble, in the order of 10 times, in phosphate ester fluid than in petroleum oils. This further accentuates the rusting problem during shut-down of the turbines and the associated control systems because, as the temperature drops during shut-down, water drops out of solution and tends to collect on components of the system with resultant rust damage.

In accordance with the present invention, a detector is provided which permits easy and frequent visual inspection to detect the presence of moisture in the system, so that the presence of moisture can be readily detected before it can cause damage to system components. This detector includes an elongated stainless steel case 20 of cylindrical or square cross section. The case 20 is provided within an elongated aperture shown at 22. While only a single aperture is illustrated in FIG. 1 and the case may be so constructed, in the preferred form a second identical aperture is provided on the opposite side of the case so that the interior may be easily viewed from both sides. The aperture 22 is covered by a window 24 of glass or other transparent material. The glass is sealed to the aperture along its edges in any suitable manner to prevent entry of foreign matter into the system through the aperture.

The case 20 is placed in communication with the hydraulic system by conduits 26 and 28. The conduits 26 and 28 are received in apertures 30 and 32, respectively, formed in the side wall 12 of the reservoir. These apertures are located above the level 16 of hydraulic fluid in the reservoir. Conduit 26 is connected to the case 20 near the top thereof and conduit 28 is connected near the bottom thereof, thereby providing a path for circulation of any moisture-containing air through the length of the elongated case. For convenience, so that the detector may be removed and replaced if necessary, the conduits 26 and 28 include unions 34 and 36, respectively, for effecting easy disconnection and reconnection. Shutoff valves 35 and 37, respectively, are provided to close the hydraulic system and prevent impurities from entering when unions 34 and 36 are opened.

In accordance with this invention, there is disposed within the case 20 in a position to be easily viewed through the windows 24 covering the apertures 22, an elongated strip 38 of material which is highly susceptible to rust in the presence of moisture. This strip 38 is supported by a hanger 40 which extends through an aperture 42 in the top of the strip.

Since upon the occurrence of significant rusting of the strip 38 it will be necessary to remove and replace this strip so that any subsequent rusting can be easily detected, provision is made for easy access to the case for this purpose. A threaded opening 44 is formed at the top end of the case 20 and a threaded plug 46 is arranged to be received in this opening 44 in sealing engagement with the top of the case. The hanger 40 is supported from the plug 46. Thus, to replace the strip 38, it is merely necessary to unscrew the plug 46, remove the strip 38 from the hanger 40 and replace it with a new strip.

In order to provide a prompt indication of the presence of moisture in the system, the strip 38 is made of a material which is highly susceptible to rust in the presence of moisture. For this purpose, any of a number of low carbon steels may be employed. In a particular embodiment of this invention, the strip 38 is formed of 1010 steel. In order to further facilitate easy visual detection of rust, indicative of moisture, on the strip, the strip is highly polished so as to present a bright surface which contrasts with any rust forming thereon.

In operation of the detector, should any significant amount of moisture of a magnitude which could cause damage to any components of the EHC system be present therein, rust quickly forms on the strip 38 and can be easily detected by a simple visual inspection by even untrained personnel. Moreover, since this inspection is of a ready visual nature and requires no time-consuming action such as a disassembly to obtain access to the reservoir for the taking of samples of the fluid and subsequent reassembly, inspection can be readily made at frequent intervals, for example, on a daily basis or more frequently if desired. Since the strip is high susceptible to rusting, any accumulation of moisture can be quickly detected and action can be taken to correct the moisture problem before any damage can result to components of the EHC system, for example, rusting of the valves thereof which could cause serious malfunctions of the system.

The detector shown in FIG. 2 is essentially the same construction as that shown in FIG. 1 except that it is modified slightly to permit mounting on the top wall 14 of the reservoir rather than on the side wall 12. A first conduit 48, corresponding generally to the conduit 26 in FIG. 1, has one end connected to an aperture in the top wall 14 of the reservoir above the level of fluid thereon. The other end of the conduit 48 is connected to the case 50, corresponding to the case 20 in FIG. 1, near the top thereof. This conduit includes a union 52 to permit disconnection of the detector. Since the conduit must extend from the top of the detector to the top of the reservoir, it is of greater length than the conduit 26. A second conduit 54, corresponding generally to the conduit 28 in FIG. 1, has one end connected to a second aperture in the top wall 14 of the reservoir above the level of fluid therein. The other end of the conduit 54 is connected to an aperture in the bottom of the case 50. A union 56 is provided in the conduit 52. As in the case of the embodiment shown in FIG. 1, the embodiment shown in FIG. 2 provides communication between the reservoir and the interior of the case 50 so that any moisture-containing air is brought into contact with the strip 38. Shutoff valves 53 and 55, respectively, are provided on the system side of unions 52 and 56 to close the system off and prevent the entry of impurities when the unions are opened.

While specific embodiments of the invention have been shown and described, it is not intended that the invention be limited to the particular constructions so shown and described since modifications will occur to those skilled in the art. For example, the case may be made entirely as a glass tube with plugs, having apertures for receiving the conduits, closing the ends of the tube. The strip employed within the case for moisture detection may be of any suitable shape instead of the elongated shape shown. Also, while it is preferred for most effective results to include two conduits as illustrated so that the moisture-containing air may circulate along the detecting strip, a single conduit of adequate size could be employed if some reduction in effectiveness can be tolerated. It is intended, therefore, to cover by the appended claims, all modifications which come within the spirit and scope of this invention.

What is claimed is:

1. In a steam turbine control system wherein hydraulic fluid is utilized to actuate steam valves the combination of:
   a. a reservoir for containing hydraulic fluid for said system;
   b. a working fluid for said system, said working fluid having a density greater than water so that any moisture which becomes admixed with said fluid will rise to the surface of said fluid in said reservoir;
   c. means for detecting the presence of water vapor in said reservoir above the level of fluid contained therein and including:
      c1. a case including transparent material permitting visual inspection of the interior of said case;
      c2. means for providing communication between the reservoir at a level above the fluid level therein and said case; and
      c3. a strip of material disposed within said case and visible through said transparent material;
      c4. said material being highly susceptible to rusting in the presence of moisture.

2. The combination of claim 1 wherein said hydraulic is a phosphate ester.

3. The combination of claim 2 wherein said material susceptible to rusting is a low carbon steel having a polished surface.

4. For use in detecting moisture in a hydraulic control system for steam turbines which includes a reservoir for fluid used in the hydraulic system, said fluid having a greater density than water a detector comprising:
   a. a case including transparent material permitting visual inspection of the interior of said case;
   b. means for providing communication between the reservoir at a level above the fluid level therein and said case; and
   c. a strip of material disposed within said case and visible through said transparent material;
   d. said material being highly susceptible to rusting in the presence of moisture.

5. The detector of claim 4, wherein said last-named material is low carbon steel.

6. The detector of claim 4, wherein said last-named material is polished 1010 steel.

7. The detector of claim 4, wherein:
   a. said detector is mounted on the side of the fluid reservoir; and
   b. wherein said means for providing communication comprises:
      i. a first conduit connected to the fluid reservoir above the level of fluid therein and connected to said case near the bottom thereof, and
      ii. a second conduit connected to the fluid reservoir above the level of fluid therein and connected to said case near the top thereof.

8. The detector of claim 4, wherein:
   a. said detector is mounted on the top of the fluid reservoir; and
   b. wherein said means for providing communication comprises:
      i. a first conduit connected to the fluid reservoir above the level of fluid therein and connected to said case at the bottom thereof, and
      ii. a second conduit connected to the fluid reservoir above the level of fluid therein and connected to said case near the top thereof.

9. The detector of claim 4, wherein:
   a. said case is of elongated shape and has an aperture extending substantially the length thereof; and
   b. a window of transparent material is positioned in said aperture and sealed to said case to permit viewing of said strip material through said window.

10. The detector of claim 4, wherein:
    a. said case is of elongated shape and has apertures on opposite sides thereof, each aperture extending substantially the length thereof; and
    b. a window of transparent material is positioned in each of said apertures and sealed to said case to permit viewing of said strip of material from either side of said case.

* * * * *